(12) United States Patent
Agrawal et al.

(10) Patent No.: US 9,440,072 B2
(45) Date of Patent: Sep. 13, 2016

(54) METHODS AND SYSTEMS FOR FITTING AN ELECTRO-ACOUSTIC STIMULATION SYSTEM TO A PATIENT

(71) Applicant: ADVANCED BIONICS AG, Staefa (CH)

(72) Inventors: Smita S. Agrawal, Stevenson Ranch, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 19 days.

(21) Appl. No.: 14/386,330

(22) PCT Filed: Mar. 22, 2013

(86) PCT No.: PCT/US2013/033604
§ 371 (c)(1),
(2) Date: Sep. 18, 2014

(87) PCT Pub. No.: WO2013/142843
PCT Pub. Date: Sep. 26, 2013

(65) Prior Publication Data
US 2015/0049890 A1 Feb. 19, 2015

Related U.S. Application Data

(60) Provisional application No. 61/614,129, filed on Mar. 22, 2012.

(51) Int. Cl.
*A61N 1/36* (2006.01)
*A61B 5/04* (2006.01)
(Continued)

(52) U.S. Cl.
CPC ....... *A61N 1/36032* (2013.01); *A61B 5/04001* (2013.01); *A61B 5/121* (2013.01);
(Continued)

(58) Field of Classification Search
CPC ........... A61N 1/36032; A61N 1/0541; H04R 25/70; H04R 2430/03; H04R 2225/67
See application file for complete search history.

(56) References Cited

U.S. PATENT DOCUMENTS 5,776,179 A 7/1998 Ren et al.
6,754,537 B1 6/2004 Harrison et al.
(Continued)

FOREIGN PATENT DOCUMENTS

WO WO-97/09863 3/1997
WO WO-2009/124165 10/2009

OTHER PUBLICATIONS

Non-Final Office Action received in U.S. Appl. No. 14/386,735 dated Jul. 20, 2015.
(Continued)

*Primary Examiner* — Curtis Kuntz
*Assistant Examiner* — Ryan Robinson
(74) *Attorney, Agent, or Firm* — ALG Intellectual Property, LLC

(57) ABSTRACT

An exemplary system includes 1) a stimulation management facility configured to direct an electro-acoustic stimulation ("EAS") system to concurrently apply acoustic stimulation to a patient by way of a loudspeaker and electrical stimulation to the patient by way of an electrode located within a cochlea of the patient during a fitting session, and 2) a fitting facility communicatively coupled to the stimulation management facility and configured to detect, during the fitting session, an interaction between the acoustic stimulation and the electrical stimulation, and set, during the fitting session, one or more control parameters governing an operation of the EAS system based on the detected interaction. Corresponding systems and methods are also disclosed.

20 Claims, 11 Drawing Sheets

(51) Int. Cl.
    *A61B 5/12* (2006.01)
    *A61N 1/05* (2006.01)
    *H04R 25/00* (2006.01)
    *A61N 1/372* (2006.01)
    *H04R 1/10* (2006.01)

(52) U.S. Cl.
    CPC ....... *A61N 1/0541* (2013.01); *A61N 1/37247* (2013.01); *H04R 1/1008* (2013.01); *H04R 25/00* (2013.01); *H04R 25/606* (2013.01); *H04R 25/70* (2013.01); *H04R 2225/67* (2013.01); *H04R 2460/03* (2013.01)

(56) References Cited

U.S. PATENT DOCUMENTS

| | | | | |
|---|---|---|---|---|
| 7,561,920 | B2* | 7/2009 | Faltys | H04R 25/70 607/55 |
| 8,086,319 | B2* | 12/2011 | van Dijk | A61N 1/36032 600/379 |
| 8,244,365 | B2* | 8/2012 | Dijk | A61N 1/36032 600/559 |
| 8,521,297 | B2* | 8/2013 | Polak | A61B 5/04001 600/559 |
| 9,155,886 | B2* | 10/2015 | James | A61N 1/36032 |
| 2004/0152946 | A1 | 8/2004 | Franck | |
| 2005/0261748 | A1 | 11/2005 | van Dijk | |
| 2007/0135862 | A1* | 6/2007 | Nicolai | A61N 1/36032 607/56 |
| 2008/0249589 | A1 | 10/2008 | Cornejo Cruz et al. | |
| 2008/0319508 | A1 | 12/2008 | Botros et al. | |
| 2009/0254149 | A1 | 10/2009 | Polak | |
| 2009/0259140 | A1 | 10/2009 | Buchman | |
| 2010/0145411 | A1 | 6/2010 | Spitzer | |
| 2010/0198301 | A1 | 8/2010 | Smith | |
| 2011/0082521 | A1 | 4/2011 | Botros et al. | |

OTHER PUBLICATIONS

Non-Final Office Action received in U.S. Appl. No. 14/386,331 dated Jul. 21, 2015.
International Search Report and Written Opinion received in International Application No. PCT/US13/033607, dated May 31, 2013.
International Search Report and Written Opinion received in International Application No. PCT/US13/033605, dated Jul. 1, 2013.
International Search Report and Written Opinion received in International Application No. PCT/US13/033604, dated Jul. 1, 2013.
Miller, Charles A., et al., "Auditory Nerve Fiber Responses to Combined Acoustic and Electric Stimulation", *Journal of the Association for Research in Otolaryngology*, Springer-Verlag, NE, vol. 10, No. 3, Feb. 10, 2009, pp. 425-445.
Payton, Lin et al., "Ipsilateral Masking Between Acoustic and Electric Stimulations", *The Journal of the Acoustical Society of America*, American Institute of Physics for the Acoustical Society of America, New York, NY, US, vol. 130, No. 2, Aug. 1, 2011, pp. 858-865.
Davis, "An Active Process in Cochlear Mechanics", *Hearing Research*, 9 (1983) 79-90, Elsevier Biomedical Press.
Kohlloffel, "Longitudinal Amplitude and Phase Distribution of the Cochlear Microphonic (Guinea Pig) and Spatial Filtering", *J. Sound Vib.* (1970) 11 (3), 325-334.
Tasaki, et al., "The Space-Time Pattern of the Cochlear Microphonics (Guinea Pig), as Recorded by Differential Electrodes", *The Journal of the Acoustical Society of America*, vol. 24, No. 5, Sep. 1952.

\* cited by examiner

METHODS AND SYSTEMS FOR FITTING AN ELECTRO-ACOUSTIC STIMULATION SYSTEM TO A PATIENT

RELATED APPLICATIONS

The present application claims priority to U.S. Provisional Patent Application No. 61/614,129, filed on Mar. 22, 2012, and entitled "Methods and Systems for Fitting an Electro-acoustic Stimulation System to a Patient," the contents of which are hereby incorporated by reference in their entirety.

BACKGROUND INFORMATION

Many hearing loss patients have some degree of residual hearing in the low frequencies (e.g., below 1 kHz) and a severe hearing loss in the high frequencies (e.g., above 1 kHz). These people cannot benefit from traditional hearing aid amplification because of the severity of the hearing loss in the high frequencies. Nor are they classic cochlear implant candidates, because of their mostly intact low frequency residual hearing.

For this group of people, electro-acoustic stimulation ("EAS") systems have been developed that provide such patients with the ability to perceive both low and high frequencies. Electro-acoustic stimulation combines the functionality of a hearing aid and a cochlear implant together in the same ear by providing acoustic stimulation representative of low frequency audio content and electrical stimulation representative of high frequency content. The auditory nerve combines the acoustic and electric stimuli into one auditory signal. Results of various studies have shown that electro-acoustic stimulation may enhance speech understanding, pitch discrimination, and music appreciation.

Unfortunately, the acoustic and electrical stimulation provided by an EAS system may sometimes negatively interact with each other, thereby degrading the listening experience of an EAS patient. For example, the electrical stimulation provided by an EAS system may have a suppressive effect on the acoustic stimulation provided by the EAS system (e.g., by preventing the neurons in the apical region of the cochlea from responding to the acoustic stimulation). Likewise, the acoustic stimulation provided by an EAS system may have a suppressive interactive effect on the electrical stimulation provided by the EAS system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
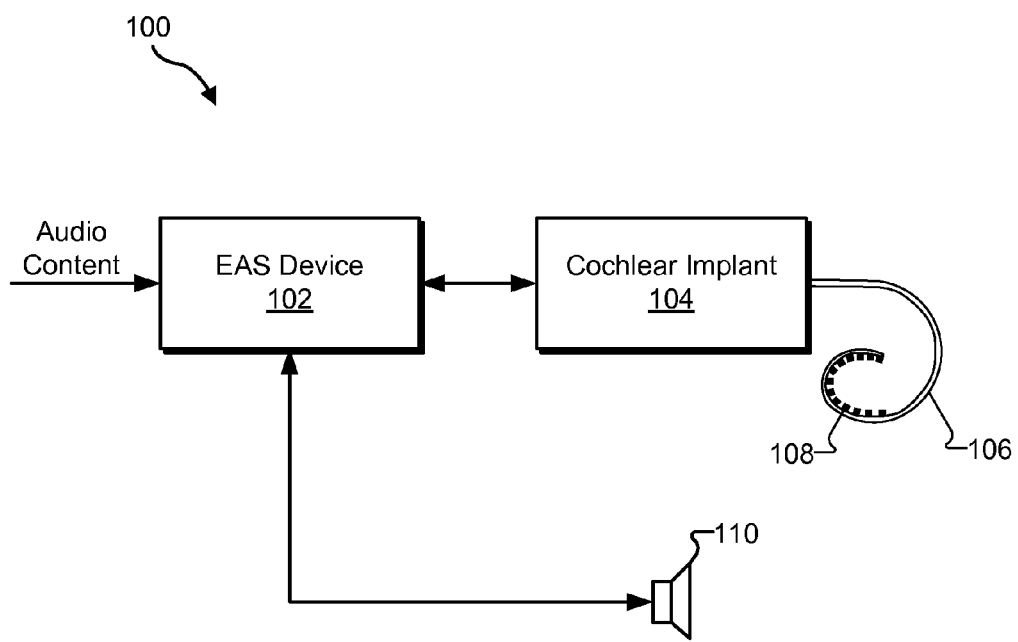
FIG. 1 illustrates an exemplary electro-acoustic stimulation ("EAS") system according to principles described herein.

Methods and systems for fitting an electro-acoustic stimulation ("EAS") system to a patient are described herein. As will be described below, a fitting system may 1) direct the EAS system to concurrently apply acoustic stimulation to a patient by way of a loudspeaker and electrical stimulation to the patient by way of an electrode located within a cochlea of the patient during a fitting session, 2) detect an interaction between the acoustic stimulation and the electrical stimulation during the fitting session, and 3) set, during the fitting session, one or more control parameters governing an operation of the EAS system based on the detected interaction.

For example, the fitting system may determine that the electrical stimulation has a suppressive interactive effect on the acoustic stimulation. Based on this determination, the fitting system may adjust one or more properties of the electrical stimulation in a manner that reduces the suppressive interactive effect of the electrical stimulation on the acoustic stimulation or disable the electrode for standard electrical stimulation subsequent to the fitting session (e.g., during one or more subsequent electro-acoustic stimulation sessions). Alternatively, the fitting system may determine that the acoustic stimulation has a suppressive interactive effect on the electrical stimulation. Based on this determination, the fitting system may adjust one or more properties of the acoustic stimulation in a manner that reduces the suppressive interactive effect of the acoustic stimulation on the electrical stimulation.

In some examples, the fitting system may determine that the electrical stimulation delivered by way of the electrode actually enhances the acoustic stimulation. In this case, as described in more detail below, the fitting system may designate the electrode as an enhancing electrode through which enhancing electrical stimulation is to be applied subsequent to the fitting session. Likewise, the fitting system may determine that the acoustic stimulation enhances the electrical stimulation delivered by way of the electrode. In this case, the fitting system may direct the EAS system to apply the acoustic stimulation every time electrical stimulation is applied by way of the electrode subsequent to the fitting session.

In some examples, the fitting system may determine that the electrical stimulation delivered by way of the electrode does not have any interactive effect on the acoustic stimulation. In this case, the fitting system may designate the electrode as an electrode through which standard electrical stimulation is to be applied subsequent to the fitting session.

As will be described below, the methods and systems described herein may facilitate an objective determination of an interactive effect that electrical stimulation has on acoustic stimulation and vice versa. As such, the methods and systems may be used to fit EAS systems to adults as well as to children and other types of patients who have difficulty providing subjective feedback during a fitting session. The methods and systems described herein may also determine (and/or aid a clinician in determining) various EAS parameters such as, but not limited to, crossover frequencies, intensity levels at the crossover frequencies, slopes of filters at the crossover frequencies, and/or other EAS parameters used to fit an EAS system to a patient.

FIG. 1 illustrates an exemplary EAS system 100. As shown, EAS system 100 may include an EAS device 102, a cochlear implant 104, an electrode lead 106 having a plurality of electrodes 108 disposed thereon, and a loudspeaker 110 (also referred to as a receiver).

EAS device 102 may include any suitable device configured to process audio content (e.g., one or more audio signals) presented to a patient and provide electrical and/or acoustic stimulation representative of the audio signals to the patient. In some examples, EAS device 102 may be implemented by an externally worn unit (e.g., a behind-the-ear device, a body worn device, etc.).

As mentioned, EAS device 102 may be used when the patient has some residual some hearing in the low frequencies (e.g., below 1000 Hz) and severe hearing loss in the high frequencies (e.g., above 1000 Hz). To this end, EAS device 102 may direct cochlear implant 104 to apply electrical stimulation representative of audio content included in a relatively high frequency band (e.g., above 1000 Hz) to one or more stimulation sites within the patient by way of one or more of electrodes 108 and loudspeaker 110 to apply acoustic stimulation representative of audio content included in a relatively low frequency band (e.g., below 1000 Hz) to the patient.

Cochlear implant 104 may include any suitable auditory prosthesis configured to be at least partially implanted within a patient as may serve a particular implementation. For example, cochlear implant 104 may include an implantable cochlear stimulator, a brainstem implant and/or any other type of auditory prosthesis. EAS device 102 and cochlear implant 104 may communicate by way of any suitable wired or wireless communication channel.

Electrode lead 106 may be implanted within the patient such that electrodes 108 are in communication with stimulation sites within the cochlea. In this configuration, EAS device 102 may direct cochlear implant 104 to apply electrical stimulation representative of an audio signal to one or more stimulation sites within the patient by way of one or more of electrodes 108. As used herein, the term "in communication with" refers to electrodes 108 being adjacent to, in the general vicinity of, in close proximity to, directly next to, or directly on the one or more stimulation sites. Any number of electrodes 108 (e.g., sixteen) may be disposed on lead 106 as may serve a particular implementation.

Figure 2:
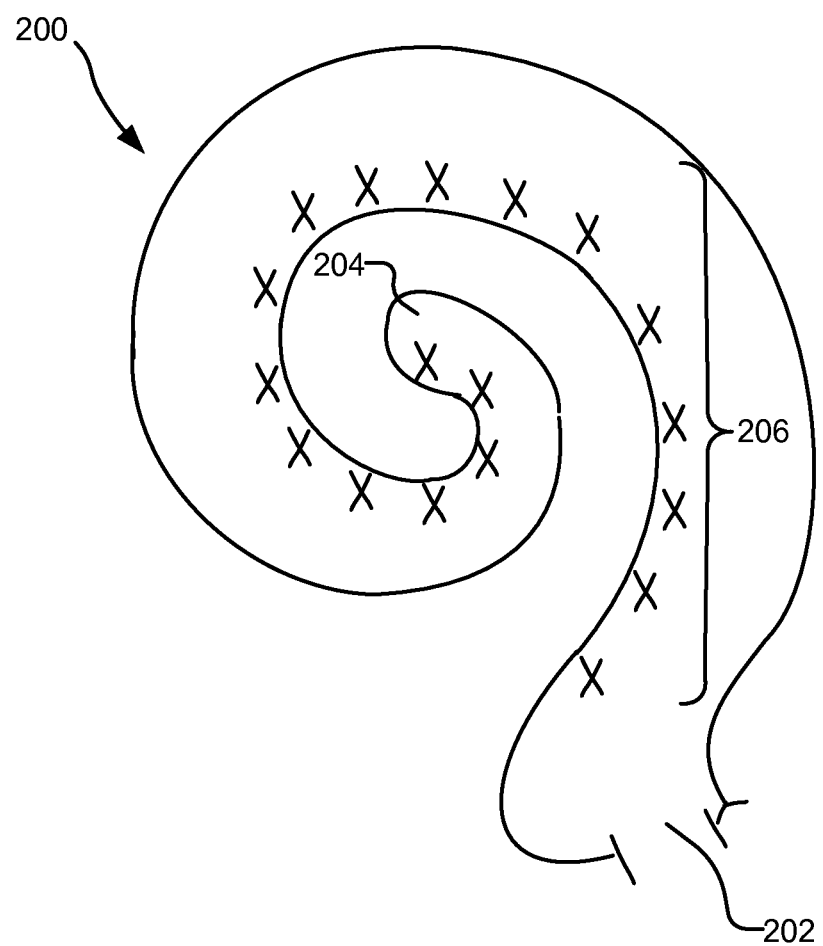
FIG. 2 illustrates a schematic structure of the human cochlea.

FIG. 2 illustrates a schematic structure of the human cochlea 200 into which lead 106 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the lead, the anatomy of the patient's cochlea, and/or any other factor as may serve a particular implementation.

Once a patient has been with EAS system 100, and during follow-up test and checkups thereafter, it may be necessary to fit EAS system 100 to the patient. Such "fitting" may include setting and/or adjustment of one or more control parameters governing an operation of EAS system 100. To facilitate fitting of EAS system 100 to a patient, a fitting system may be selectively and communicatively coupled to EAS system 100. As will be described below, the fitting system may additionally or alternatively be implemented by EAS device 102.

Figure 3:
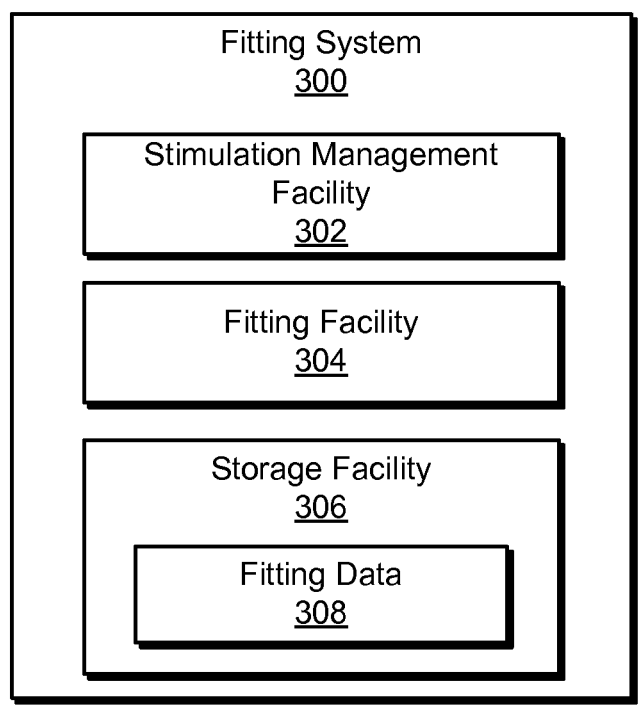
FIG. 3 illustrates an exemplary fitting system according to principles described herein.

FIG. 3 illustrates an exemplary fitting system 300. As shown in FIG. 3, fitting system 300 may include a stimulation management facility 302, a fitting facility 304, and a storage facility 306, which may be in communication with one another using any suitable communication technologies. One or more of facilities 302-306 may include one or more computing devices and/or processors configured to perform one or more of the functions described herein. Facilities 302-306 will now be described in more detail.

Stimulation management facility 302 may be configured to perform one or more acoustic and/or electrical stimulation management operations. For example, stimulation management facility 302 may be configured to direct, during a fitting session, an EAS system (e.g., EAS system 100) to concurrently apply acoustic stimulation to a patient by way of a loudspeaker (e.g., loudspeaker 110 or any other suitable transducer, headphone, earphone, and/or specialized hearing aid) and electrical stimulation to the patient by way of an electrode (e.g., one of electrodes 108) located within a cochlea of the patient. As used herein, a "fitting session" refers to a period of time during which one or more fitting operations are performed. The acoustic and electrical stimulation may have any suitable characteristic as may serve a particular implementation. For example, the acoustic stimulation may include a relatively low frequency tone burst (e.g., a 125 Hz tone burst) and the electrical stimulation may include monopolar stimulation. The electrode to which the electrical stimulation is applied may be any electrode located within the cochlea of the patient (e.g., the most apical electrode).

Fitting facility 304 may be configured to perform one or more fitting operations associated with an EAS system (e.g., EAS system 100). For example, fitting facility 304 may detect an interaction between the acoustic stimulation and the electrical stimulation applied by an EAS system at the direction of stimulation management facility 302. Fitting facility 304 may then set one or more control parameters governing an operation of the EAS system based on the detected interaction.

Storage facility 306 may be configured to maintain fitting data 308 generated and/or utilized by stimulation management facility 302 and/or fitting facility 304. Storage facility 306 may be configured to maintain additional or alternative data as may serve a particular implementation.

Various examples of detecting an interaction between acoustic and electrical stimulation and then setting one or more control parameters governing an operation of an EAS system based on the detected interaction will now be described.

In some examples, fitting facility 304 may determine an interactive effect that the electrical stimulation has on the acoustic stimulation and set one or more electrical stimulation control parameters governing an operation of the EAS system based on the determined interactive effect. As used herein, "electrical stimulation control parameters" refer to control parameters that govern a manner in which an EAS system applies electrical stimulation by way of one or more electrodes disposed within a cochlea of a patient.

Fitting facility 304 may determine an interactive effect that the electrical stimulation has on the acoustic stimulation in any suitable manner. To illustrate, fitting facility 304 may determine an interactive effect that the electrical stimulation has on the acoustic stimulation by measuring an evoked response that occurs in response to the concurrent application of the acoustic stimulation and the electrical stimulation and comparing the evoked response to a baseline response that occurs in response to an application of the acoustic stimulation by itself. As used herein, an "evoked response" refers to an intracochlear hair-cell response (i.e., cochlear microphonics), a neural response (e.g., an auditory nerve response, a brainstem response, a compound action potential), and/or any other type of neural or physiological response that may occur within a patient in response to application of acoustic and/or electrical stimulation to the patient. A "baseline response" refers to an evoked response that occurs in response to application of a single type of stimulus (e.g., acoustic stimulation only).

Figure 4:
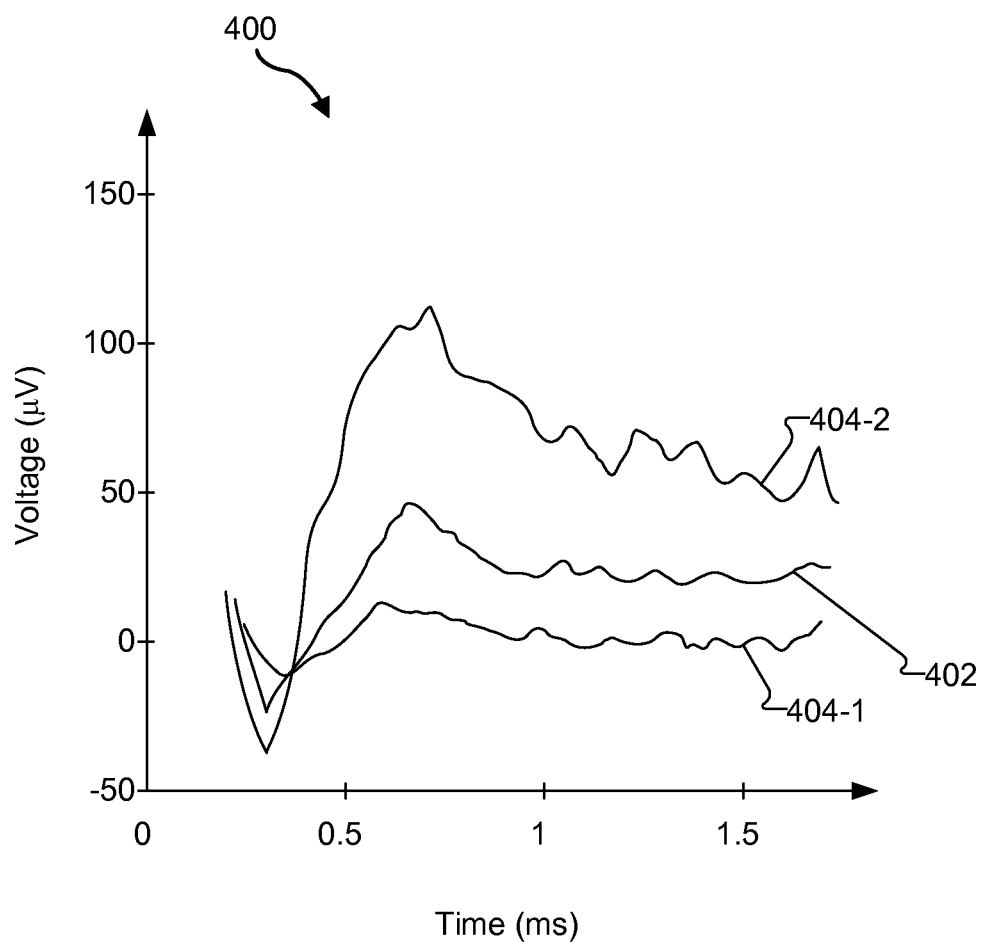
FIG. 4 shows an exemplary baseline response that may occur in response to application of acoustic stimulation by itself and two possible evoked responses that may occur in response to concurrent application of the same acoustic stimulation together with electrical stimulation according to principles described herein.

To illustrate, FIG. 4 shows an exemplary baseline response 402 that may occur in response to application of acoustic stimulation by itself and two possible evoked responses 404-1 and 404-2 that may occur in response to concurrent application of the same acoustic stimulation together with electrical stimulation. As shown, evoked response 404-1 is less than baseline response 402 (i.e., evoked response 404-1 has a steady state amplitude that is less than a steady state amplitude of baseline response 402). Hence, if concurrent application of the acoustic and electrical stimulation results in an evoked response similar to evoked response 404-1 (i.e., if the evoked response is less than baseline response 402), fitting facility 304 may determine that the electrical stimulation has a suppressive interactive effect on the acoustic stimulation. Conversely, evoked response 404-2 is greater than baseline response 402 (i.e., evoked response 404-2 has a steady state amplitude that is greater than a steady state amplitude of baseline response 402). Hence, if concurrent application of the acoustic and electrical stimulation results in an evoked response similar to evoked response 404-2 (i.e., if the evoked response is greater than baseline response 402), fitting facility 304 may determine that the electrical stimulation has an enhancing interactive effect on the acoustic stimulation.

A baseline response (e.g., baseline response 402) may be measured or determined by fitting facility 304 in any suitable manner. For example, fitting facility 304 may measure a baseline response that occurs in response to application of acoustic stimulation by directing an EAS system to apply the acoustic stimulation, recording an evoked response that occurs in response to the application of the acoustic stimulation, designating the evoked response that occurs in response to the application of the acoustic stimulation as the baseline response, and storing data representative of the baseline response. The acoustic stimulation used to elicit the baseline response may include any suitable type of acoustic stimulation as may serve a particular implementation. For example, the acoustic stimulation used to elicit the baseline response may include a relatively low frequency tone burst (e.g., a 125 Hz tone burst).

An evoked response may be recorded in any suitable manner using any suitable combination of recording electrodes. For example, an intracochlear hair-cell response (cochlear microphonics) may be recorded using one or more electrodes positioned within the cochlea (e.g., one or more of electrodes 108), one or more electrodes positioned within the round window, and/or one or more electrodes positioned at any other suitable location relatively near the cochlea. Likewise, an auditory nerve response and/or a compound action potential may be recorded using one or more electrodes positioned within or near the cochlea. It will be recognized that the electrodes used to record the evoked response may be disposed on a lead that has been inserted into the cochlea (e.g., lead 106) and/or on a fly lead that has been positioned at any other suitable location within the patient.

An evoked response may be recorded in any suitable manner using any suitable combination of recording electrodes. For example, an intracochlear hair-cell response may be recorded in accordance with one or more cochlear microphonics techniques using one or more electrodes positioned within the cochlea (e.g., one or more of electrodes 108), one or more electrodes positioned within the round window, and/or one or more electrodes positioned at any other suitable location relatively near the cochlea. Likewise, an auditory nerve response and/or a compound action potential may be recorded using one or more electrodes positioned within or near the cochlea. It will be recognized that the electrodes used to record the evoked response may be disposed on a lead that has been inserted into the cochlea (e.g., lead 106) and/or on a fly lead that has been positioned at any other suitable location within the patient.

In some examples, one or more electrodes located external to the patient may be used to record an evoked response. For example, a brainstem response may be recorded using one or more non-invasive electrodes that have been affixed externally to the head of the patient.

Additionally or alternatively, fitting facility 304 may determine an interactive effect that the electrical stimulation has on the acoustic stimulation based on subjective feedback provided by the patient. For example, fitting facility 304 may direct the EAS system to first present only the acoustic stimulation to the patient. Immediately thereafter, fitting facility 304 may direct the EAS system to concurrently present the same acoustic stimulation together with electrical stimulation to the patient. A clinician may ask the patient to compare the two types of stimulation (i.e., the acoustic stimulation by itself versus acoustic stimulation together with electrical stimulation). In response, the patient may indicate that one type of stimulation was louder, clearer, or otherwise different than the other type of stimulation. In response to this subjective feedback, the clinician may provide data representative of the interactive effect that the electrical stimulation has on the acoustic stimulation to fitting facility 304 (e.g., by way of one or more graphical user interfaces provided by fitting facility 304).

As another example, fitting facility 304 may determine an interactive effect that the electrical stimulation has on the acoustic stimulation by performing a spectral ripple test with respect to the ear associated with the EAS system. During an exemplary spectral ripple test, a spectral ripple test score is generated for the ear that indicates the smallest spectral contrast of a spectrally modulated stimulus that the ear is capable of detecting. Exemplary spectral ripple tests that may be used in accordance with the methods and systems described herein are described more fully in U.S. Pat. No. 8,027,734, which patent is incorporated herein by reference in its entirety.

To illustrate, a spectral ripple test may be performed by determining the smallest spectral contrast of a spectrally modulated acoustic stimulus that the ear is capable of detecting with and without the concurrent application of an electrical stimulus. If the spectral ripple test score improves in the presence of the electrical stimulus, fitting facility 304 may determine that the electrical stimulation has an enhancing interactive effect on the acoustic stimulation. Conversely, if the spectral ripple test score decreases in the presence of the electrical stimulus, fitting facility 304 may determine that the electrical stimulation has a suppressive interactive effect on the acoustic stimulation. If the spectral ripple test score does not change in the presence of the electrical stimulus, fitting facility 304 may determine that the electrical stimulation does not have either a suppressive or an enhancing interactive effect on the acoustic stimulation.

Once fitting facility 304 has determined the type of interactive effect that the electrical stimulation has on the acoustic stimulation (i.e., whether the electrical stimulation has a suppressive interactive effect, an enhancing interactive effect, or no interactive effect on the acoustic stimulation), fitting facility 304 may set one or more electrical stimulation control parameters governing an operation of the EAS system based on the determined interactive effect.

To illustrate, fitting facility 304 may determine that the electrical stimulation has a suppressive interactive effect on the acoustic stimulation. In response, fitting facility 304 may adjust one or more properties of the electrical stimulation in a manner that reduces the suppressive interactive effect of the electrical stimulation on the acoustic stimulation. For example, the intensity level, pulse width, and/or rate of the electrical stimulation may be adjusted until the suppressive interactive effect is minimized. It will be recognized that any other characteristic of the electrical stimulation may be adjusted in order to minimize the suppressive interactive effect of the electrical stimulation on the acoustic stimulation as may serve a particular implementation. Fitting facility 304 may then direct the EAS system to limit the type of electrical stimulation provided by way of the electrode subsequent to the fitting session to that defined by the adjusted one or more parameters.

In some alternative examples, fitting facility 304 may designate the electrode through which the suppressive electrical stimulation is applied as being disabled subsequent to the fitting session. In this manner, electrical stimulation will not be applied by way of the designated electrode during normal operation of the EAS system (i.e., while the EAS system is operating in a non-fitting mode). Rather, acoustic stimulation will be used to represent sound within the frequency range associated with the electrode.

In some examples, fitting facility 304 may first adjust one or more properties of the electrical stimulation provided by way of a particular electrode in an attempt to reduce (e.g., minimize or eliminate) the suppressive interactive effect that the electrical stimulation has on the acoustic stimulation. If fitting facility 304 determines that adjustment of the one or more properties of the electrical stimulation does not satisfactorily reduce the suppressive interactive effect of the electrical stimulation on the acoustic stimulation, fitting facility 304 may then designate the electrode as being disabled subsequent to the fitting session.

To illustrate, fitting facility 304 may determine that electrical stimulation provided by way of the most apical electrode has a suppressive interactive effect on the acoustic stimulation. In response, fitting facility 304 may adjust one or more properties of the electrical stimulation provided by way of the most apical electrode. If this adjustment does not reduce the suppressive interactive effect of the electrical stimulation on the acoustic stimulation (which may be determined by recording one or more additional evoked responses after the one or more properties have been adjusted), fitting facility 304 may designate the most apical electrode as being disabled subsequent to the fitting session.

In some examples, fitting facility 304 may determine that the electrical stimulation delivered by way of a particular electrode has an enhancing interactive effect on the acoustic stimulation. In response, fitting facility 304 may designate the electrode as an enhancing electrode through which enhancing electrical stimulation is to be applied subsequent to the fitting session.

As used herein, "enhancing stimulation" refers to any type of electrical stimulation configured to enhance acoustic stimulation. For example, enhancing stimulation may include sub-threshold electrical stimulation (i.e., electrical stimulation that has a stimulation level that is less than a threshold level required for the patient to perceive the electrical stimulation). Concurrent application of sub-threshold electrical stimulation by way of an electrode together with acoustic stimulation may enhance the acoustic stimulation in a variety of ways. For example, the sub-threshold electrical stimulation may lower an acoustic detection threshold of the patient. As used herein, an "acoustic detection threshold" of a patient refers to a sound level of acoustic stimulation that is required for the patient to detect the acoustic stimulation. Hence, the sub-threshold electrical stimulation may make it easier for the patient to detect the acoustic stimulation. Sub-threshold electrical stimulation may additionally or alternatively serve to maintain patency (i.e., inhibit neuropathy) of hearing nerve cells located in the region of the cochlea that is associated with the electrode.

The EAS system may apply enhancing stimulation by way of the designated enhancing electrode in any suitable way. For example, EAS device 102 may direct cochlear implant 104 to apply steady-state electrical stimulation by way of the designated electrode during the application of the acoustic stimulation. As another example, EAS device 102 may direct cochlear implant 104 to apply sporadic electrical stimulation by way of the designated electrode during the application of the acoustic stimulation. As another example, EAS device 102 may direct cochlear implant 104 to apply periodic electrical stimulation by way of the designated electrode during the application of the acoustic stimulation. Each type of enhancing stimulation may include monopolar, bipolar, multipolar, and/or any other type of electrical stimulation as may serve a particular implementation.

In some examples, fitting facility 304 may determine that the electrical stimulation delivered by way of a particular electrode does not have either a suppressive or enhancing interactive effect on the acoustic stimulation. In this case, fitting facility 304 may designate the electrode as an electrode through which standard electrical stimulation is to be applied subsequent to the fitting session. As used herein, "standard electrical stimulation" refers to electrical stimulation used to represent audio content presented to the patient. Hence, electrical stimulation may be applied by way of the designated electrode to represent audio content having a frequency included within a range of frequencies associated with that electrode.

Figure 5:
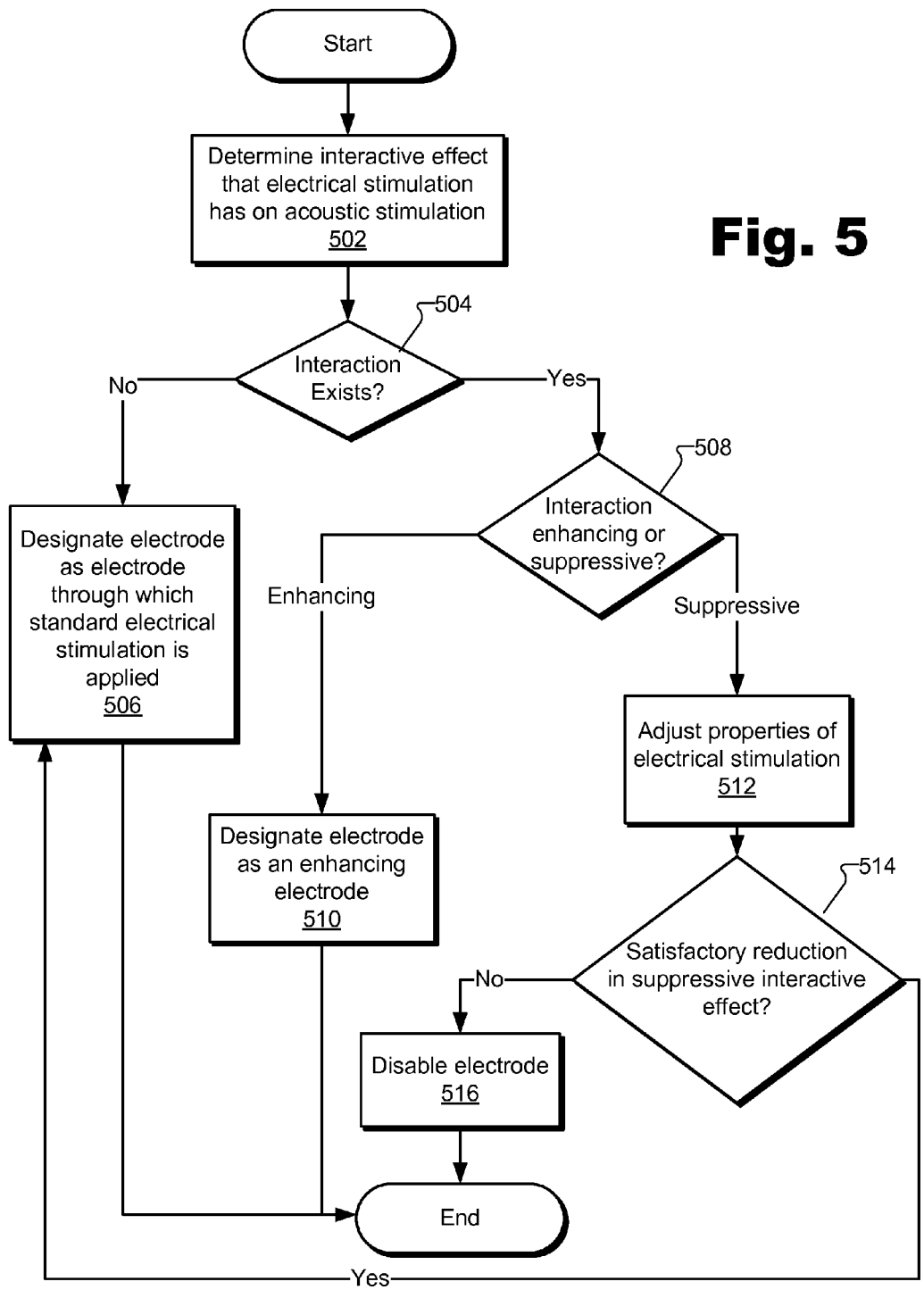
FIG. 5 is a flowchart illustrating an exemplary method of evaluating and accounting for an interactive effect that electrical stimulation may have on acoustic stimulation in an EAS system according to principles described herein.

FIG. 5 is a flowchart illustrating an exemplary method of evaluating and accounting for an interactive effect that electrical stimulation may have on acoustic stimulation in an EAS system. While FIG. 5 illustrates exemplary steps according to one embodiment, other embodiments may omit, add to, reorder, and/or modify any of the steps shown in FIG. 5. One or more of the steps shown in FIG. 5 may be performed by fitting system 300 or any implementation thereof during a fitting session.

In step 502, a fitting system determines an interactive effect that electrical stimulation delivered by way of a particular electrode has on acoustic stimulation that is concurrently delivered to a patient. Step 502 may be performed in any of the matters described herein. For example, step 502 may be performed objectively (e.g., by measuring one or more evoked responses elicited by concurrent application of the acoustic and electrical stimulation) or subjectively (e.g., by applying a spectral ripple test to the patient).

In step 504, the fitting system determines whether an interaction between the electrical stimulation and the acoustic stimulation exists. If there is no interaction (i.e., the electrical stimulation does not have an interactive effect on the acoustic stimulation), the fitting system designates the electrode as an electrode through which standard electrical stimulation is to be applied subsequent to the fitting session in step 506.

If the fitting system determines that an interaction between the electrical stimulation and the acoustic stimulation exists, the fitting system determines whether the interaction is enhancing or suppressive in step 508. If the interaction is enhancing (i.e., the electrical stimulation has an enhancing effect on the acoustic stimulation), the fitting system designates the electrode as an enhancing electrode in step 510. However, if the interaction is suppressive (i.e., the electrical stimulation has a suppressive effect on the acoustic stimulation), the fitting system may adjust one or more properties of the electrical stimulation in step 512. If a satisfactory reduction in the suppressive interactive effect is realized by the adjustment of the one or more properties of the electrical stimulation (Yes; step 514), the fitting system designates the electrode as an electrode through which standard electrical stimulation is to be applied subsequent to the fitting session (i.e., step 506). However, if a satisfactory reduction in a suppressive interactive effect is not realized by the adjustment of the one or more properties of the electrical stimulation (No; step 514), the fitting system disables the electrode in step 516.

Returning to FIG. 3, in some examples, fitting facility 304 may determine an interactive effect that the acoustic stimulation has on the electrical stimulation and set one or more acoustic stimulation control parameters governing an operation of the EAS system based on the determined interactive effect. As used herein, "acoustic stimulation control parameters" refer to control parameters that govern a manner in which an EAS system applies acoustic stimulation to a patient.

Fitting facility 304 may determine an interactive effect that the acoustic stimulation has on the electrical stimulation in any suitable manner. To illustrate, fitting facility 304 may determine an interactive effect that the acoustic stimulation has on the electrical stimulation by measuring an evoked response that occurs in response to the concurrent application of the acoustic stimulation and the electrical stimulation and comparing the evoked response to a baseline response that occurs in response to an application of the electrical stimulation by itself.

For example, if the evoked response is greater than the baseline response, fitting facility 304 may determine that the acoustic stimulation has an enhancing interactive effect on the electrical stimulation. Conversely, if the evoked response is less than the baseline response, fitting facility 304 may determine that the acoustic stimulation has a suppressive interactive effect on the electrical stimulation. If the evoked response is substantially equal to the baseline response, fitting facility 304 may determine that the acoustic stimulation has substantially no interactive effect on the electrical stimulation. It will be recognized that the evoked response and baseline response may be generated and measured in a manner that is similar to that described above in connection with FIG. 4.

In some examples, fitting facility 304 may determine an interactive effect that the acoustic stimulation has on the electrical stimulation based on subjective feedback provided by the patient. This may be performed in a similar manner as that described above.

Once fitting facility 304 has determined the type of interactive effect that the acoustic stimulation has on the electrical stimulation (i.e., whether the acoustic stimulation has a suppressive interactive effect, an enhancing interactive effect, or no interactive effect on the electrical stimulation), fitting facility 304 may set one or more acoustic stimulation control parameters governing an operation of the EAS system based on the determined interactive effect.

To illustrate, fitting facility 304 may determine that the acoustic stimulation has a suppressive interactive effect on the electrical stimulation. In response, fitting facility 304 may adjust one or more properties of the acoustic stimulation in a manner that reduces the suppressive interactive effect of the acoustic stimulation on the electrical stimulation. For example, the intensity level, duration, and/or frequency of the acoustic stimulation may be adjusted until the suppressive interactive effect is minimized. It will be recognized that any other characteristic of the acoustic stimulation may be adjusted in order to minimize the suppressive interactive effect of the acoustic stimulation on the electrical stimulation as may serve a particular implementation.

In some examples, if the adjustment of the one or more properties of the acoustic stimulation does not result in a satisfactory reduction in the suppressive interactive effect, fitting facility 304 may direct the EAS system to not apply the acoustic stimulation while the electrical stimulation is delivered subsequent to the fitting session (i.e., during a normal operation of the EAS system).

As another example, fitting facility 304 may determine that the acoustic stimulation has an enhancing interactive effect on the electrical stimulation. In response, fitting facility 304 may direct the EAS system to apply the acoustic stimulation while the electrical stimulation is delivered subsequent to the fitting session (i.e., during a normal operation of the EAS system).

In some examples, fitting facility 304 may determine that the acoustic stimulation does not have either a suppressive or enhancing interactive effect on the electrical stimulation. In this case, fitting facility 304 directs the EAS system to not apply the acoustic stimulation while the electrical stimulation is delivered subsequent to the fitting session (i.e., during a normal operation of the EAS system). This may allow the EAS system to conserve power during normal operation.

While the functions of determining an interactive effect that the electrical stimulation has on the acoustic stimulation and determining an interactive effect that the acoustic stimulation has on the electrical stimulation have been described separately, it will be recognized that fitting facility 304 may concurrently determine the interactive effect that each type of stimulation has on the other. Fitting facility 304 may then set one or more electrical and/or acoustic stimulation parameters based on the determined interactive effect.

In some examples, fitting facility 304 may determine an optimal crossover frequency associated with the acoustic stimulation and the electrical stimulation based on the detected interaction between the acoustic stimulation and the electrical stimulation. As used herein, a "crossover frequency" refers to a boundary frequency that separates frequencies represented to the patient by acoustic stimulation and frequencies represented to the patient by electrical stimulation. For example, fitting facility 304 may determine that acoustic stimulation evokes a robust hair cell and neural responses until 450 Hz, the apical most electrode can start providing stimulation around that frequency, provided there is no suppression of the acoustic response. In case suppression is observed, the fitting system may adjust one or more properties of the electrical stimulation as was the case in step 512. If a satisfactory reduction in the suppressive interactive effect is realized by the adjustment of the one or more properties of the electrical stimulation (Yes; step 514), the fitting system designates the electrode as an electrode through which standard electrical stimulation is to be applied subsequent to the fitting session. However, if a satisfactory reduction in a suppressive interactive effect is not realized by the adjustment of the one or more properties of the electrical stimulation (No; step 514), the fitting system disables the electrode in step 516. The next electrode is then selected to provide stimulation around 450 Hz provided there are no suppressive effects observed again. Various other properties (e.g., intensity levels at the crossover frequency, a slope of one or more filters at the crossover frequency, and/or other EAS parameters used to fit an EAS system to a patient) associated with the crossover frequency may also be determined based on the detected interaction.

Fitting system 300 may be implemented by one or more components of EAS system 100. For example, fitting system 300 may be implemented entirely by EAS device 102. To illustrate, EAS device 102 may periodically analyze an interaction that occurs between acoustic and electrical stimulation and adjust one or more control parameters accordingly. In this case, the term "fitting session" may refer to the period of time during which EAS device 102 performs the analysis.

Figure 6:
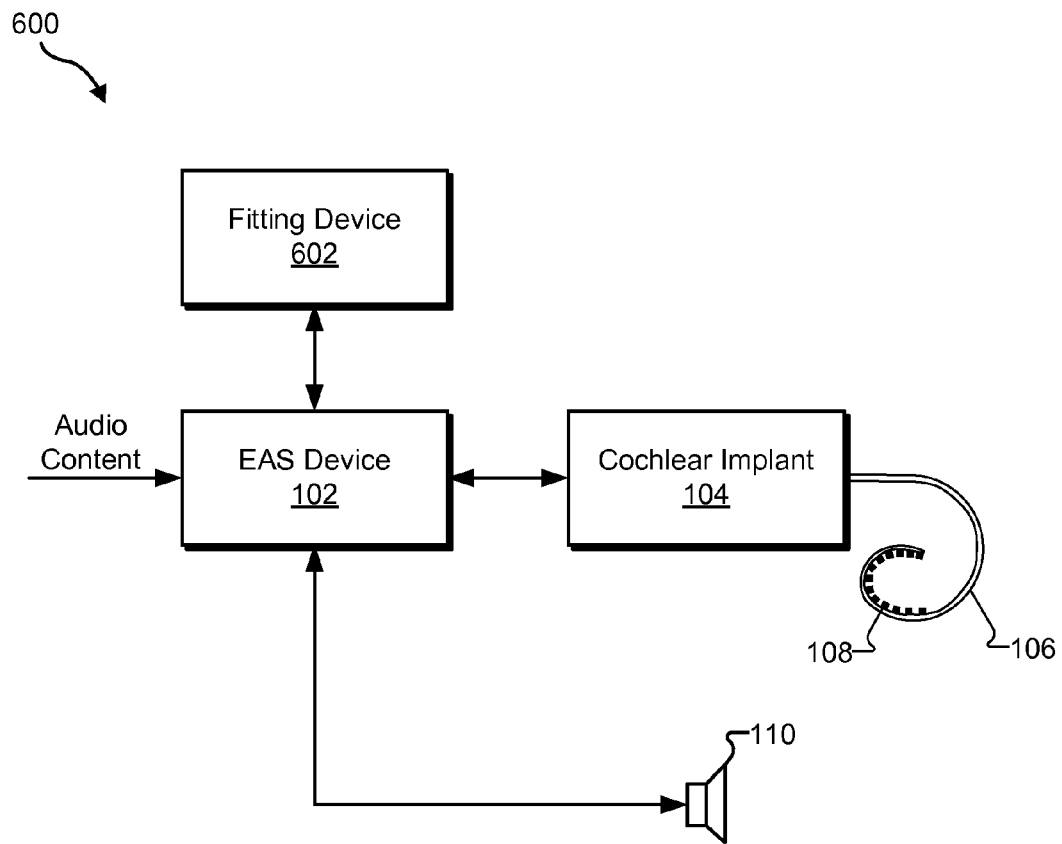
FIG. 6 shows an exemplary configuration in which the fitting system of FIG. 3 is at least partially implemented by a fitting device communicatively coupled to an EAS device according to principles described herein.

Alternatively, fitting system 300 may be at least partially implemented by a fitting device selectively and communicatively coupled to EAS device 102. To illustrate, FIG. 6 shows an exemplary configuration 600 in which fitting system 300 is at least partially implemented by a fitting device 602 communicatively coupled to EAS device 102. Fitting device 602 may implemented by any suitable combination of computing and communication devices including, but not limited to, a fitting station, a personal computer, a laptop computer, a handheld device, a mobile device (e.g., a mobile phone), and/or any other suitable component as may serve a particular implementation. In some examples, fitting device 602 may provide one or more graphical user interfaces ("GUIs") with which a clinician or other user may interface in order to fit EAS system 100 to the patient.

Figure 7:
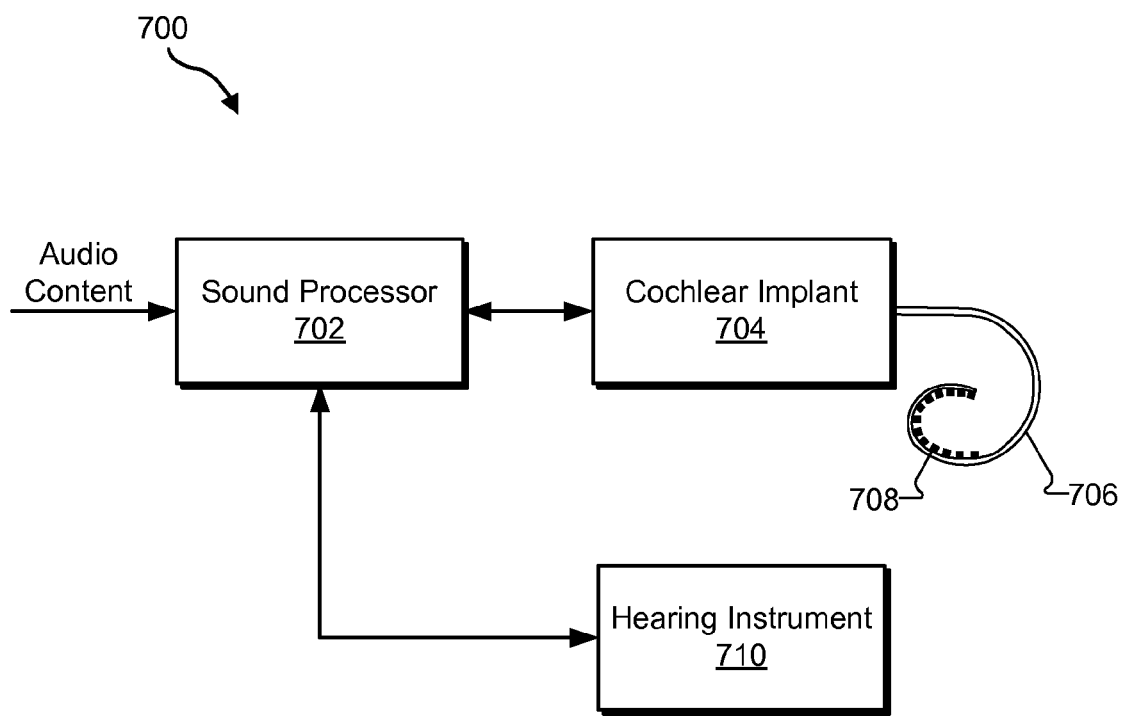
FIG. 7 illustrates an exemplary bimodal cochlear implant system according to principles described herein.

In some examples, fitting system 300 may be used to understand and evaluate interactions between acoustic and electrical stimulation in a bimodal cochlear implant system. FIG. 7 illustrates an exemplary bimodal cochlear implant system 700 that may be used by a bimodal cochlear implant patient (i.e., a patient fitted with a cochlear implant for one ear and an acoustic hearing instrument for the other ear). As shown, bimodal cochlear implant system 700 may include a sound processor 702, a cochlear implant 704, and an electrode lead 706 having a plurality of electrodes 708 disposed thereon. Bimodal cochlear implant system 700 may also include a hearing instrument 710 communicatively coupled to sound processor 702. Hearing instrument 710 may include any type of acoustic hearing aid as may serve a particular implementation.

Cochlear implant 704 may be used to apply electrical stimulation to one of the ears of the patient and hearing instrument 710 may be used to apply acoustic stimulation to the other ear of the patient. Both cochlear implant 704 and hearing instrument 710 may be controlled by sound processor 702, which may receive and process audio content.

In some examples, fitting system 300 may be used to detect and evaluate interactions between the ipsilateral (same ear) or contralateral (opposite ear) acoustic stimulation provided by hearing instrument 710 and the electrical stimulation provided by cochlear implant 704. To this end, fitting system 300 may be at least partially implemented by sound processor 702 and/or a fitting device (which may be similar to fitting device 602) selectively and communicatively coupled to sound processor 702.

Figure 8:
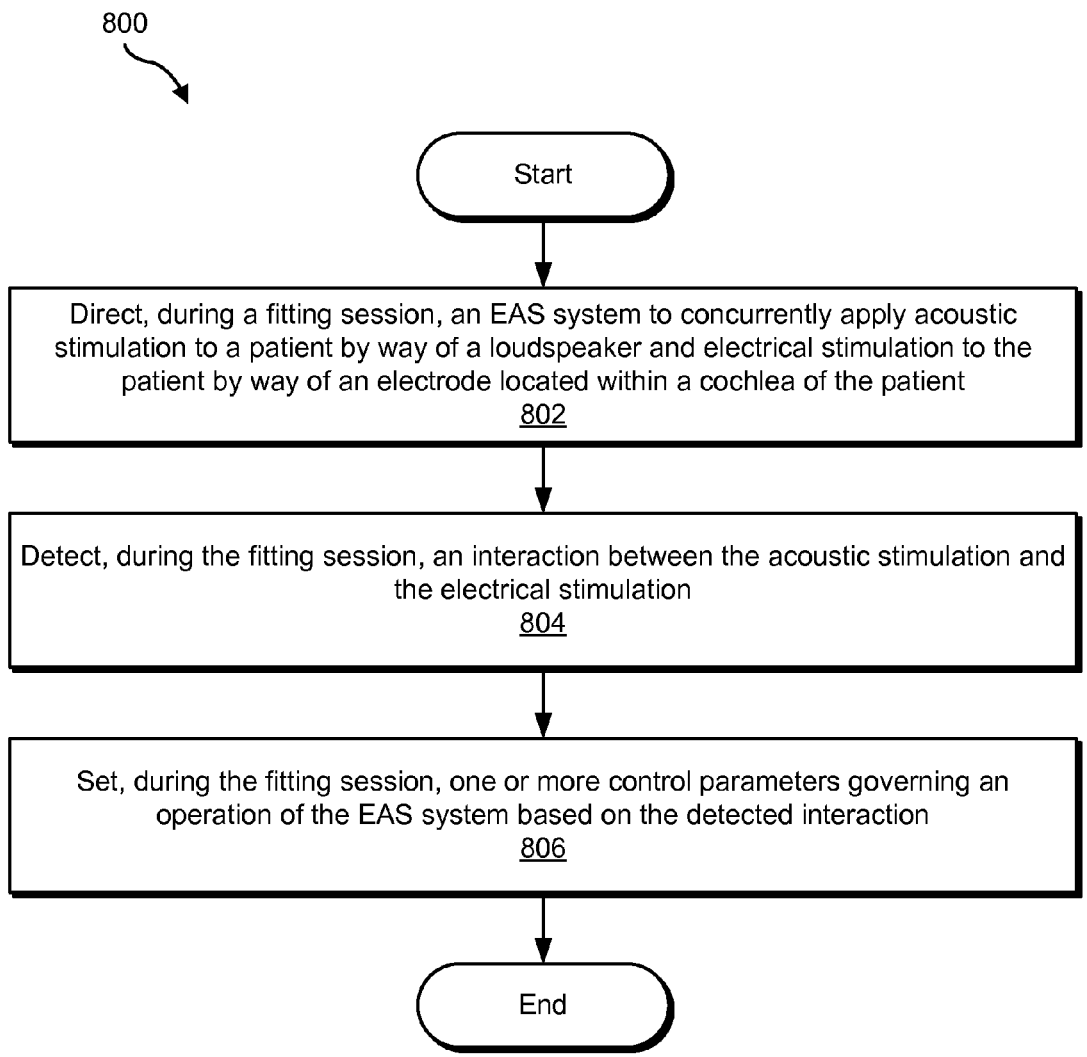
FIG. 8 illustrates an exemplary method of fitting an EAS system to a patient according to principles described herein.

FIG. 8 illustrates an exemplary method 800 of fitting an EAS system to a patient. While FIG. 8 illustrates exemplary steps according to one embodiment, other embodiments may omit, add to, reorder, and/or modify any of the steps shown in FIG. 8. One or more of the steps shown in FIG. 8 may be performed by fitting system 300 and/or any implementation thereof.

In step 802, a fitting system directs, during a fitting session, an EAS system to concurrently apply acoustic stimulation to a patient by way of a loudspeaker and electrical stimulation to the patient by way of an electrode located within a cochlea of the patient. Step 802 may be performed in any of the ways described herein.

In step 804, the fitting system detects, during the fitting session, an interaction between the acoustic stimulation and the electrical stimulation. Step 804 may be performed in any of the ways described herein.

In step 806, the fitting system sets, during the fitting session, one or more control parameters governing an operation of the EAS system based on the detected interaction. Step 806 may be performed in any of the ways described herein.

Figure 9:
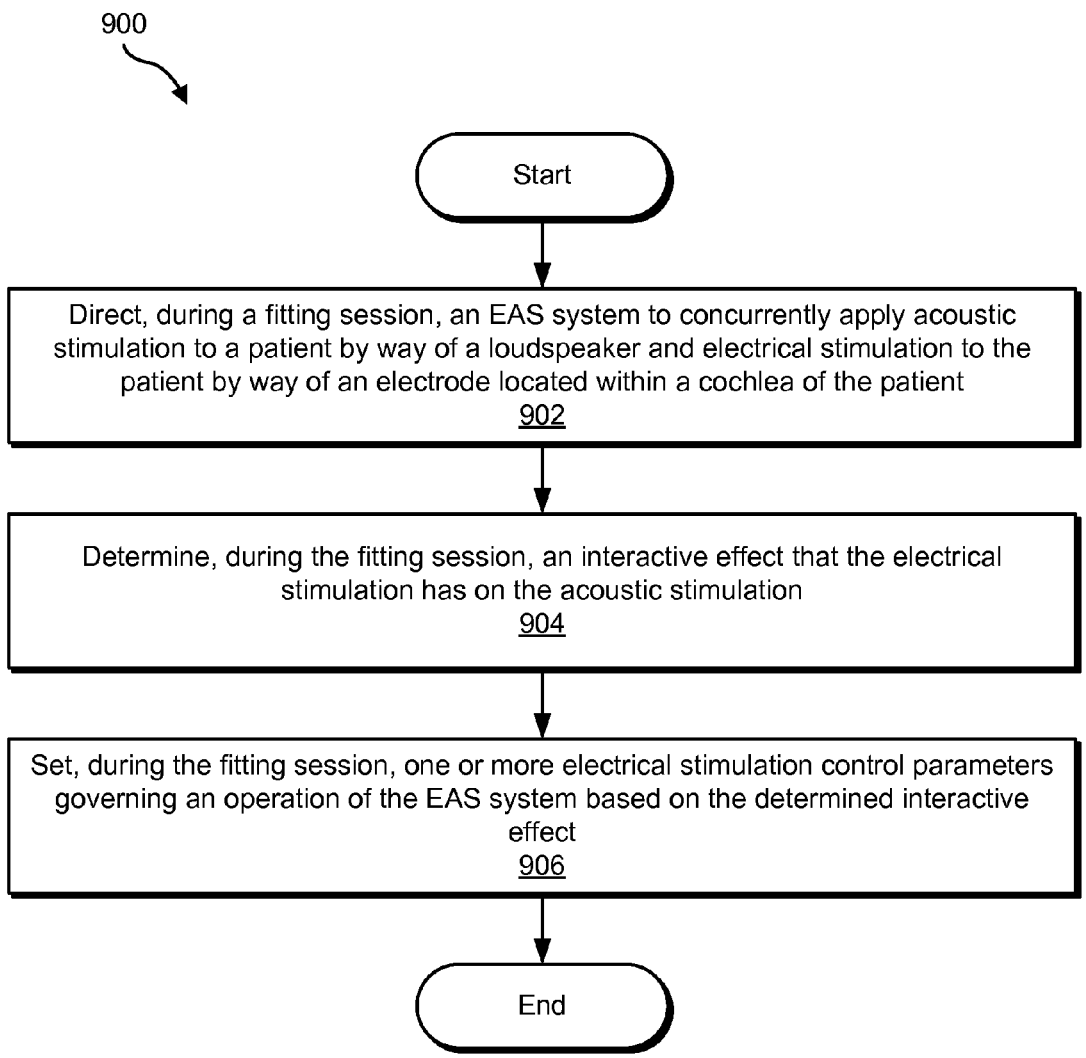
FIG. 9 illustrates another exemplary method of fitting an EAS system to a patient according to principles described herein.

FIG. 9 illustrates another exemplary method 900 of fitting an EAS system to a patient. While FIG. 9 illustrates exemplary steps according to one embodiment, other embodiments may omit, add to, reorder, and/or modify any of the steps shown in FIG. 9. One or more of the steps shown in FIG. 9 may be performed by fitting system 300 and/or any implementation thereof.

In step 902, a fitting system directs, during a fitting session, an EAS system to concurrently apply acoustic stimulation to a patient by way of a loudspeaker and electrical stimulation to the patient by way of an electrode located within a cochlea of the patient. Step 902 may be performed in any of the ways described herein.

In step 904, the fitting system determines, during the fitting session, an interactive effect that the electrical stimulation has on the acoustic stimulation. Step 904 may be performed in any of the ways described herein.

In step 906, the fitting system sets, during the fitting session, one or more electrical stimulation control parameters governing an operation of the EAS system based on the determined interactive effect. Step 906 may be performed in any of the ways described herein.

Figure 10:
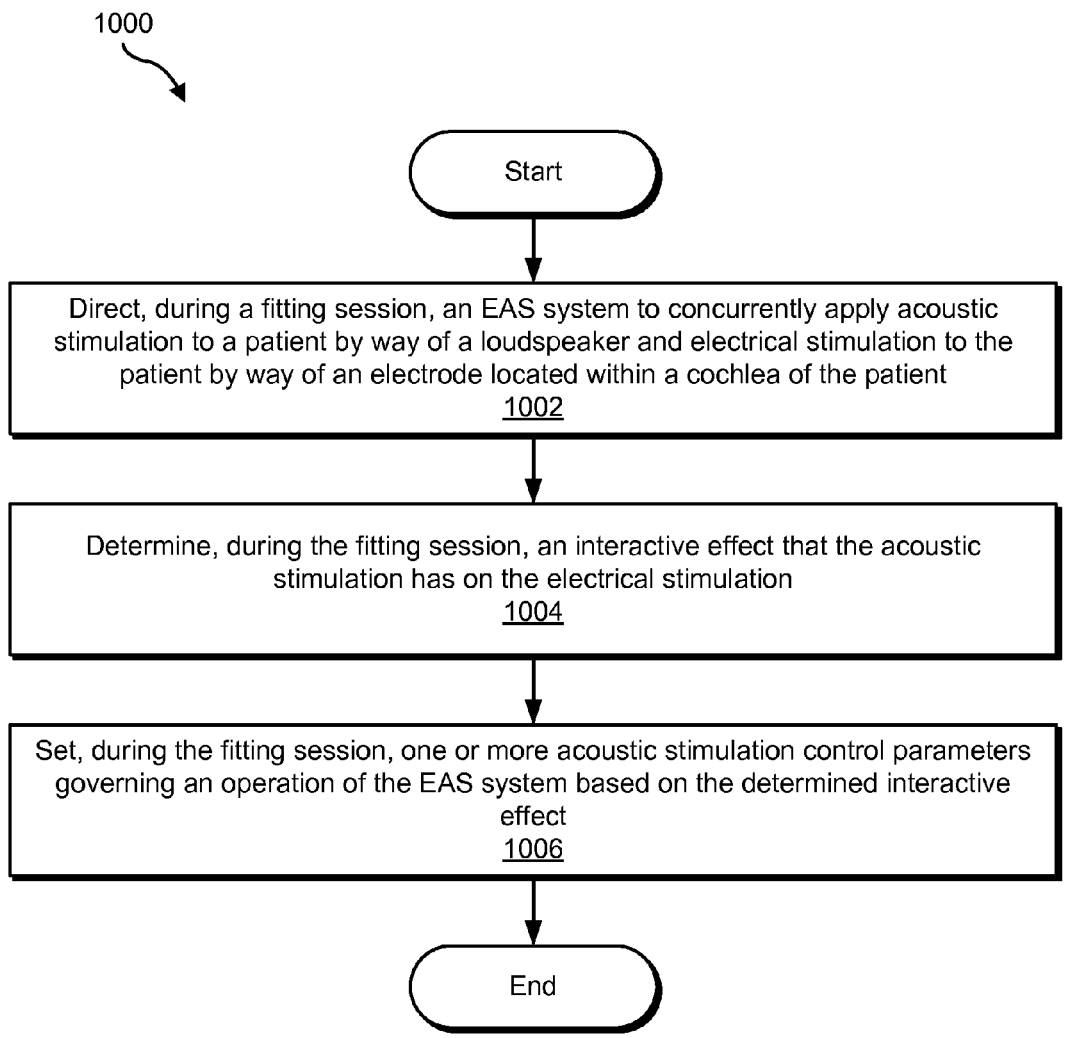
FIG. 10 illustrates another exemplary method of fitting an EAS system to a patient according to principles described herein.

FIG. 10 illustrates another exemplary method 1000 of fitting an EAS system to a patient. While FIG. 10 illustrates exemplary steps according to one embodiment, other embodiments may omit, add to, reorder, and/or modify any of the steps shown in FIG. 10. One or more of the steps shown in FIG. 10 may be performed by fitting system 300 and/or any implementation thereof.

In step 1002, a fitting system directs, during a fitting session, an EAS system to concurrently apply acoustic stimulation to a patient by way of a loudspeaker and electrical stimulation to the patient by way of an electrode located within a cochlea of the patient. Step 1002 may be performed in any of the ways described herein.

In step 1004, the fitting system determines, during the fitting session, an interactive effect that the acoustic stimulation has on the electrical stimulation. Step 1004 may be performed in any of the ways described herein.

In step 1006, the fitting system sets, during the fitting session, one or more acoustic stimulation control parameters governing an operation of the EAS system based on the determined interactive effect. Step 1006 may be performed in any of the ways described herein.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 11:
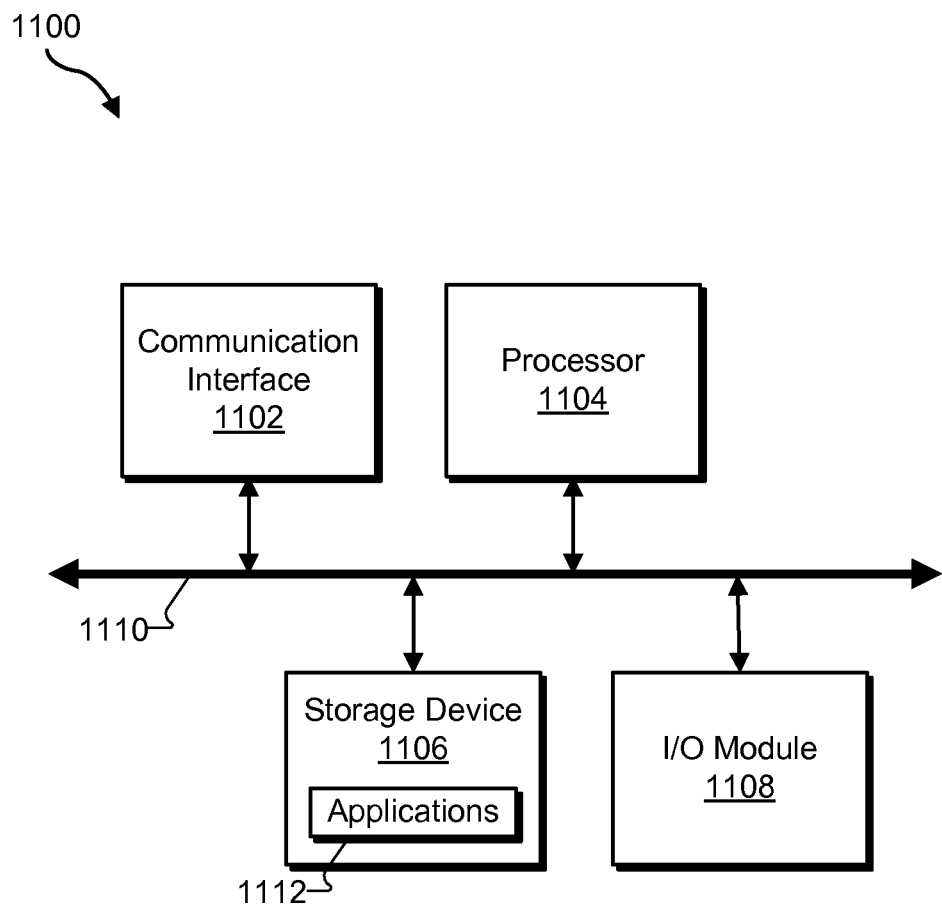
FIG. 11 illustrates an exemplary computing device according to principles described herein.

FIG. 11 illustrates an exemplary computing device 1100 that may be configured to perform one or more of the processes described herein. As shown in FIG. 11, computing device 1100 may include a communication interface 1102, a processor 1104, a storage device 1106, and an input/output ("I/O") module 1108 communicatively connected via a communication infrastructure 1110. While an exemplary computing device 1100 is shown in FIG. 11, the components illustrated in FIG. 11 are not intended to be limiting. Additional or alternative components may be used in other embodiments. Components of computing device 1100 shown in FIG. 11 will now be described in additional detail.

Communication interface 1102 may be configured to communicate with one or more computing devices. Examples of communication interface 1102 include, without limitation, a wired network interface (such as a network interface card), a wireless network interface (such as a wireless network interface card), a modem, an audio/video connection, and any other suitable interface.

Processor 1104 generally represents any type or form of processing unit capable of processing data or interpreting, executing, and/or directing execution of one or more of the instructions, processes, and/or operations described herein. Processor 1104 may direct execution of operations in accordance with one or more applications 1112 or other computer-executable instructions such as may be stored in storage device 1106 or another computer-readable medium.

Storage device 1106 may include one or more data storage media, devices, or configurations and may employ any type, form, and combination of data storage media and/or device. For example, storage device 1106 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1106. For example, data representative of one or more executable applications 1112 configured to direct processor 1104 to perform any of the operations described herein may be stored within storage device 1106. In some examples, data may be arranged in one or more databases residing within storage device 1106.

I/O module 1108 may be configured to receive user input and provide user output and may include any hardware, firmware, software, or combination thereof supportive of input and output capabilities. For example, I/O module 1108 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1108 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1108 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1100. For example, one or more applications 1112 residing within storage device 1106 may be configured to direct processor 1104 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a stimulation management facility configured to direct, during a fitting session, an electro-acoustic stimulation ("EAS") system comprising an EAS device communicatively coupled to both a loudspeaker and a cochlear implant to concurrently apply acoustic stimulation to a patient by way of the loudspeaker and electrical stimulation to the patient by way of an electrode communicatively coupled to the cochlear implant and located within a cochlea of the patient; and
a fitting facility communicatively coupled to the stimulation management facility and configured to
detect, during the fitting session, an interaction between the acoustic stimulation and the electrical stimulation, and
set, during the fitting session, one or more control parameters governing an operation of the EAS system based on the detected interaction.

2. The system of claim 1, wherein the interaction between the acoustic stimulation and the electrical stimulation results in the acoustic stimulation being suppressed by the electrical stimulation, and wherein the fitting facility is configured to set the one or more control parameters by adjusting the one or more control parameters in a manner that reduces the suppression of the acoustic stimulation by the electrical stimulation.

3. The system of claim 1, wherein the interaction between the acoustic stimulation and the electrical stimulation results in the acoustic stimulation being suppressed by the electrical stimulation, and wherein the fitting facility is configured to set the one or more control parameters by designating the electrode as being disabled subsequent to the fitting session.

4. The system of claim 1, wherein the interaction between the acoustic stimulation and the electrical stimulation results in the acoustic stimulation being enhanced by the electrical stimulation, and wherein the fitting facility is configured to set the one or more control parameters by designating the electrode as an enhancing electrode through which enhancing electrical stimulation is to be applied subsequent to the fitting session.

5. The system of claim 1, wherein the interaction between the acoustic stimulation and the electrical stimulation results in the electric stimulation being suppressed by the acoustic stimulation, and wherein the fitting facility is configured to set the one or more control parameters by adjusting the one or more control parameters in a manner that reduces the suppression of the electric stimulation by the acoustic stimulation.

6. The system of claim 1, wherein the fitting facility is further configured to determine an optimal crossover frequency associated with the acoustic stimulation and the electrical stimulation based on the detected interaction.

7. A system comprising:
a stimulation management facility configured to direct, during a fitting session, an electro-acoustic stimulation ("EAS") system comprising an EAS device communicatively coupled to both a loudspeaker and a cochlear implant to concurrently apply acoustic stimulation to a patient by way of the loudspeaker and electrical stimulation to the patient by way of an electrode communicatively coupled to the cochlear implant and located within a cochlea of the patient; and
a fitting facility communicatively coupled to the stimulation management facility and configured to
determine, during the fitting session, an interactive effect that the electrical stimulation has on the acoustic stimulation, and
set, during the fitting session, one or more electrical stimulation control parameters governing an operation of the EAS system based on the determined interactive effect.

8. The system of claim 7, wherein:
the fitting facility is configured to determine the interactive effect by determining that the electrical stimulation has a suppressive interactive effect on the acoustic stimulation; and
the fitting facility is configured to set the one or more electrical stimulation control parameters by adjusting one or more properties of the electrical stimulation in a manner that reduces the suppressive interactive effect of the electrical stimulation on the acoustic stimulation.

9. The system of claim 7, wherein:
the fitting facility is configured to determine the interactive effect by determining that the electrical stimulation has a suppressive interactive effect on the acoustic stimulation; and
the fitting facility is configured to set the one or more electrical stimulation control parameters by designating the electrode as being disabled subsequent to the fitting session.

10. The system of claim 7, wherein:
the fitting facility is configured to determine the interactive effect by determining that the electrical stimulation has an enhancing interactive effect on the acoustic stimulation; and
the fitting facility is configured to set the one or more electrical stimulation control parameters by designating the electrode as an enhancing electrode through which enhancing electrical stimulation is to be applied subsequent to the fitting session.

11. The system of claim 7, wherein:
the fitting facility is configured to determine the interactive effect by determining that the electrical stimulation does not have either a suppressive or enhancing interactive effect on the acoustic stimulation; and
the fitting facility is configured to set the one or more electrical stimulation control parameters by designating the electrode as an electrode through which standard electrical stimulation is to be applied subsequent to the fitting session.

12. The system of claim 7, wherein the fitting facility is configured to determine the interactive effect by:
recording an evoked response that occurs in response to the concurrent application of the acoustic stimulation and the electrical stimulation; and
comparing the evoked response to a baseline response that occurs in response to an application of the acoustic stimulation by itself;
wherein, if the evoked response is greater than the baseline response, the fitting determines that the electrical stimulation has an enhancing interactive effect on the acoustic stimulation; and
wherein, if the evoked response is less than the baseline response, the fitting facility determines that the electrical stimulation has a suppressive interactive effect on the acoustic stimulation.

13. The system of claim 12, wherein the evoked response comprises at least one of an intracochlear hair-cell response and a neural response.

14. The system of claim 12, wherein the fitting facility is further configured to measure, prior to the recording of the evoked response that occurs in response to the concurrent application of the acoustic stimulation and the electrical stimulation, the baseline response by:
  directing the EAS system to apply the acoustic stimulation;
  recording an evoked response that occurs in response to the application of the acoustic stimulation; and
  designating the evoked response that occurs in response to the application of the acoustic stimulation as the baseline response.

15. The system of claim 7, wherein the fitting facility is configured to determine the interactive effect by determining the interactive effect based on subjective feedback provided by the patient.

16. A system comprising:
  a stimulation management facility configured to direct, during a fitting session, an electro-acoustic stimulation ("EAS") system comprising an EAS device communicatively coupled to both a loudspeaker and a cochlear implant to concurrently apply acoustic stimulation to a patient by way of the loudspeaker and electrical stimulation to the patient by way of an electrode communicatively coupled to the cochlear implant and located within a cochlea of the patient; and
  a fitting facility communicatively coupled to the stimulation management facility and configured to
    determine, during the fitting session, an interactive effect that the acoustic stimulation has on the electrical stimulation, and
    set, during the fitting session, one or more acoustic stimulation control parameters governing an operation of the EAS system based on the determined interactive effect.

17. The system of claim 16, wherein:
  the fitting facility is configured to determine the interactive effect by determining that the acoustic stimulation has a suppressive interactive effect on the electrical stimulation; and
  the fitting facility is configured to set the one or more acoustic stimulation control parameters by adjusting one or more properties of the acoustic stimulation in a manner that reduces the suppressive interactive effect of the acoustic stimulation on the electrical stimulation.

18. The system of claim 16, wherein the fitting facility is configured to determine the interactive effect by:
  recording an evoked response that occurs in response to the concurrent application of the acoustic stimulation and the electrical stimulation; and
  comparing the evoked response to a baseline response that occurs in response to an application of the electrical stimulation by itself;
  wherein, if the evoked response is greater than the baseline response, the fitting facility determines that the acoustic stimulation has an enhancing interactive effect on the electrical stimulation; and
  wherein, if the evoked response is less than the baseline response, the fitting facility determines that the acoustic stimulation has a suppressive interactive effect on the electrical stimulation.

19. The system of claim 18, wherein the fitting facility is further configured to measure, prior to the recording of the evoked response that occurs in response to the concurrent application of the acoustic stimulation and the electrical stimulation, the baseline response by:
  applying the electrical stimulation;
  recording an evoked response that occurs in response to the application of the electrical stimulation; and
  designating the evoked response that occurs in response to the application of the electrical stimulation as the baseline response.

20. A method comprising:
  directing, by a fitting system during a fitting session, an electro-acoustic stimulation ("EAS") system comprising an EAS device communicatively coupled to both a loudspeaker and a cochlear implant to concurrently apply acoustic stimulation to a patient by way of the loudspeaker and electrical stimulation to the patient by way of an electrode communicatively coupled to the cochlear implant and located within a cochlea of the patient;
  detecting, by the fitting system during the fitting session, an interaction between the acoustic stimulation and the electrical stimulation; and
  setting, by the fitting system during the fitting session, one or more control parameters governing an operation of the EAS system based on the detected interaction.

* * * * *